(12) United States Patent
Bellani et al.

(10) Patent No.: US 6,340,760 B1
(45) Date of Patent: Jan. 22, 2002

(54) PROCESS FOR THE PREPARATION OF (S)-N-TERT-BUTYL-1,2,3,4-TETRAHYDROISOQUINOLINE-3-CARBOXYAMIDE

(75) Inventors: Pietro Bellani; Marco Frigerio, both of Milan (IT)

(73) Assignee: Clariant LSM Italia S.p.A, Origgio (IT)

( * ) Notice: Subject to any disclaimer, the term of this patent is extended or adjusted under 35 U.S.C. 154(b) by 0 days.

(21) Appl. No.: 09/478,690

(22) Filed: Jan. 6, 2000

Related U.S. Application Data

(63) Continuation of application No. PCT/EP99/04266, filed on Jun. 17, 1999.

(30) Foreign Application Priority Data

Jun. 26, 1998 (IT) .......................... MI98A1478

(51) Int. Cl.[7] .................... C07D 491/048; C07D 491/04
(52) U.S. Cl. .................... 546/89; 546/146; 546/147
(58) Field of Search .................. 546/89, 146

(56) References Cited

U.S. PATENT DOCUMENTS 5,587,481 A * 12/1996 Allen et al. ................. 546/146

FOREIGN PATENT DOCUMENTS

EP        0 751 128    *  1/1997  ................. 546/146

OTHER PUBLICATIONS

The Merck Index, Twelfth Edition, pp. 1438–39, 1996.*

* cited by examiner

*Primary Examiner*—Alan L. Rotman
(74) *Attorney, Agent, or Firm*—Darby & Darby

(57) ABSTRACT

A description is given here of a novel process for the synthesis of N-carboxyanhydride of formula VI

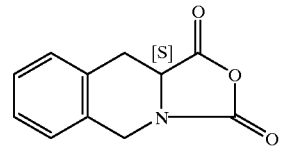

by reacting (3S)-1,2,3,4-tetrahydroisoquinoline-3-carboxylic acid with triphosgene in dioxane; a description is also given of a process for the synthesis of (S)-N-tert-butyl-1,2,3,4-tetrahydroisoquinoline-3-carboxamide by treating the N-carboxyanhydride VI so obtained with tert-butylamine.

16 Claims, No Drawings

PROCESS FOR THE PREPARATION OF (S)-N-TERT-BUTYL-1,2,3,4-TETRAHYDROISOQUINOLINE-3-CARBOXYAMIDE

This Application is a continuation of PCT/E99/04266 filed Jun. 17, 1999.

The present invention relates to a novel process for the preparation of N-carboxyanhydride (NCA) of formula VI

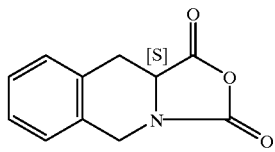

V by reacting (3S)-1,2,3,4-tetrahydroisoquinoline-3-carboxylic acid VII

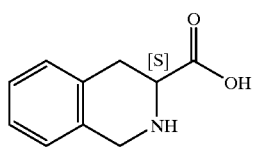

VI with triphosgene in dioxane. N-carboxyanhydride VI is an intermediate of primary importance in the preparation of (S)-N-tert-butyl-1,2,3,4-tetrahydroisoquinoline-3-carboxyamide I, the structural formula of which is given below

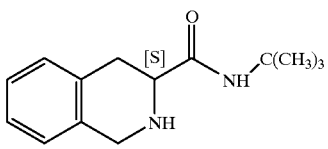

I and which, in its turn, is a key intermediate in the preparation of compounds that have a high pharmacological activity and that can be used in particular in the treatment and prevention of infections caused by HIV.

In the majority of known anti-viral drugs, carboxyamide I is not used directly as such but is previously hydrogenated to give N-tert-butyl-decahydro-(4aS,8aS)-isoquinoline-3 (S)-carboxyamide of formula II

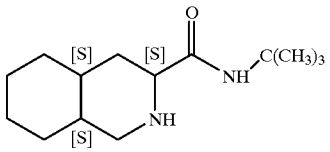

II which, by suitable substitutions at the isoquinoline nitrogen which will be obvious to any person skilled in the art, is in turn converted into the pharmacologically active derivative. In U.S. Pat. No. 5,196,438, a description is given precisely of pharmacologically active compounds having an anti-viral activity, the structural formula of which is given below

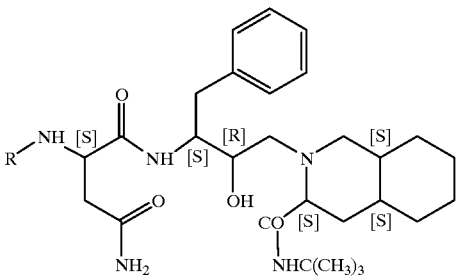

II in which the decahydroisoquinoline residue derived from carboxyamide II is immediately identifiable; among these, the derivative of most interest, and the structural formula of which is given below,

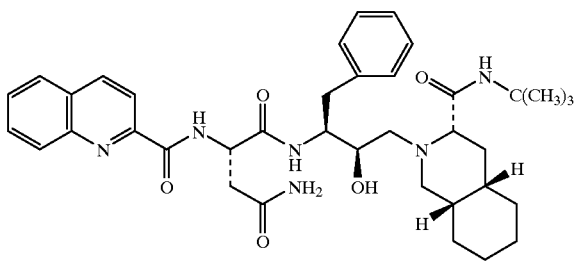

is known by the commercial name Saquinavir.

Another anti-viral drug of substantial importance, which also contains the decahydroisoquinoline residue present in Saquinavir, is Nelfinavir, the structural formula of which is likewise given below

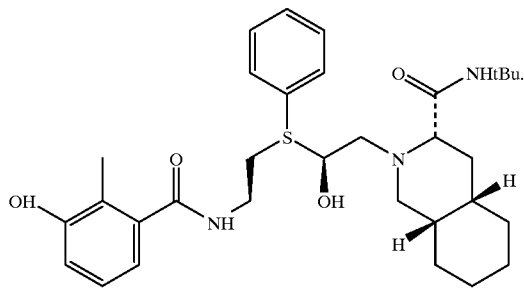

Both Nelfinavir and Saquinavir are normally used in the form of the corresponding water-soluble salts and, in particular, in the form of the mesylated salts. European Patent Application EP 533000 describes a synthesis process in which a compound of formula IV

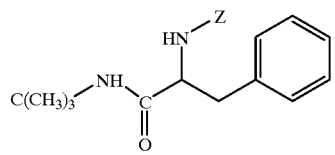

I wherein Z=benzyloxycarbonyl, is reacted with formaldehyde in acetic acid and in the presence of sulphuric acid to give the compound V

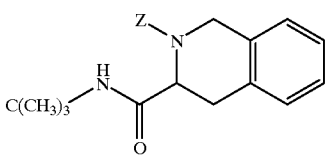

which is then converted into carboxyamide I by removing the benzyloxycarbonyl group.

That synthesis is, however, of little industrial interest because it is distinguished by relatively modest yields.

U.S. Pat. No. 5,587,481 describes a process in which (3S)-1,2,3,4-tetrahydroisoquinoline-3-carboxylic acid VII is reacted with phosgene to give the N-carboxyanhydride (NCA) of formula VI which is then reacted directly with tert-butylamine with the consequent formation of carboxyamide I; the solvents indicated for carrying out the conversion of VII into VI are tetrahydrofuran (THF), dioxane, ethyl acetate, butyl acetate and isopropyl acetate, although ethyl acetate is the only solvent mentioned in the Examples.

Although the process described in U.S. Pat. No. 5,587,481 is faster and more profitable than that described in EP 533000, it nevertheless has not inconsiderable disadvantages. First among these is the fact that it uses phosgene which is a highly dangerous toxic gas, the use of which is now strictly regulated in most industrialised countries, both for reasons of safety at work and, above all, for reasons of environmental safety.

It should also be emphasised that the yields of the process in question are nevertheless relatively modest: carboxyamide I is in fact produced with a yield of from 74 to 84%, while the total yield of the process which leads to the formation of amide II is from 47 to 56%.

European Patent Application EP 751128 describes a similar synthesis process in which the conversion of compound VII into compound VI can be effected either with phosgene or with triphosgene.

The advantages resulting from the process described in EP 751128 are clear because the use of triphosgene which, unlike phosgene, is not a toxic gas, permits complete safety of implementation with a consequent saving in operating costs and plant costs; triphosgene is also a solid compound which enables it to be used more accurately and therefore without the typical secondary reactions which may occur with the use of a gaseous reagent in excess. In this second case, the solvent used for the conversion of VII into VI is THF, which can be used either as the only solvent or in admixture with methylene chloride.

It should be noted in this connection that, in EP 751128, the use of triphosgene is limited solely to laboratory scale production (Example 1) with final yields in terms of compound I of 84.7%. However, as regards production on an industrial scale, or at least in a pilot plant, only synthesis by means of phosgene with final yields, still in terms of compound I, of 72.5% (Example 2) is mentioned.

It has, however, now been established, as shown by the data given in Table 1 (Sample E), that the use of triphosgene to convert compound VII into compound VI is really a process limited to the laboratory scale only (5–20 g); on a larger scale (100–1000 g) falls in yield occur such as to prejudice its use at an industrial level. It has also been established that the use of ethyl acetate, as taught in U.S. Pat. No. 5,587,481, is not compatible with the use of triphosgene, even for production on a laboratory scale (see Table 1-Sample A).

The object of the present invention is therefore to optimise the conversion of compound VII into compound VI by reaction with triphosgene, identifying a suitable solvent which is capable of permitting the reproduction, with high yields, of the above-mentioned reaction even on an industrial scale.

It has now been found, and this constitutes the subject-matter of the present invention, that by effecting the reaction of (3S)-1,2,3,4-tetrahydroisoquinoline-3-carboxylic acid (VII) with triphosgene in dioxane, the formation of the N-carboxyanhydride of formula VI takes place with substantially identical and equally high yields both when operating at a laboratory level and when operating on an industrial scale.

The fact that the production of compound VI by reacting compound VII with triphosgene in dioxane can be carried out with substantially identical yields both at a laboratory level and at an industrial level is, per se, a very surprising phenomenon, above all in view of the disparity encountered when operating in THF instead.

In the routine practice of organic chemistry THF and dioxane are normally regarded as entirely equivalent solvents (J. March, *Advanced Organic Chemistry*, J. Wiley & Sons, $4^{th}$ Ed., pages 357–362), in particular precisely with regard to the production of -NCA by means of phosgene (Kricheldorf, "-Amino-N-Carboxyanhydrides and Related Heterocycles" Springer Verlag, N.Y., 1987, pages 1–58); on the basis of the prior art, therefore, it would have been reasonable to expect a substantial fall in terms of yield also when operating in dioxane.

Instead, as will be appreciated from the Examples given below, carboxyamide VI is obtained with substantially quantitative yields by effecting the reaction of acid VII with triphosgene in dioxane; in particular, the carboxyamide VI so obtained can then be converted into (S)-N-tert-butyl-1,2,3,4-tetrahydroisoquinoline-3-carboxyamide with final yields of from 84 to 85% by carrying out the reaction on from 5 to 100 g of starting acid VII, and with final yields of 82% by carrying out the reaction on 100 kg of acid VII, that is to say, on a typically industrial scale.

The present invention therefore relates also to:
1. the process for the production of (S)-N-tert-butyl-1,2,3,4-tetrahydroisoquinoline-3-carboxyamide comprising the reaction of (3S)-1,2,3,4-tetrahydroisoquinoline-3-carboxylic acid with triphosgene in dioxane;
2. the processes for the production of anti-viral drugs, in particular Nelfinavir and Saquinavir, and of the corresponding salt derivatives, which processes in their turn comprise said reaction of (3S)-1,2,3,4-tetrahydroisoquinoline-3-carboxylic acid with triphosene in dioxane.

In the preferred embodiment of the present invention, (3S)-1,2,3,4-tetrahydroisoquinoline-3-carboxylic acid VII is treated in dioxane at an initial concentration of from 0.3 to 2.0 m/l, preferably from 0.5 to 1.5 m/l, with from 0.3 to 1.2 equivalents of triphosgene at temperatures of from +20 to +105° C., preferably with reflux of the reaction mixture.

The optional second stage of the process, that is to say, corresponding to the opening of the intermediate VI to give (S)-N-tert-butyl-1,2,3,4-tetrahydroisoquinoline-3-carboxyamide, is carried out in an inert organic solvent, preferably toluene, THF, dioxane, methylene chloride, even more preferably in toluene, operating at a temperature of from −20 to +30° C., preferably from −10 to +5° C., and adding from 1 to 10 equivalents, preferably from 3 to 5 equivalents, of tert-butylamine.

The end product is then isolated in accordance with conventional techniques, preferably by crystallisation. The crystallisation can be carried out by solvents such as acetone, methanol, ethanol, n-propanol, isopropanol, water and mixtures thereof; isopropanol is the preferred solvent for effecting the crystallisation.

(S)-N-tert-butyl-1,2,3,4-tetrahydroisoquinoline-3-carboxyamide I can then be hydrogenated to N-tert-butyl-decahydro-(4aS,8aS)-isoquinoline-3(S)-carboxyamide II in accordance with conventional techniques in the presence of a reduction catalyst in heterogeneous phase, preferably rhodium supported on alumina; the hydrogenation is normally carried out in an organic polar solvent, preferably an alcohol, even more preferably isopropanol.

Those and other aspects of the invention will become clear from the following Examples which are to be regarded purely as non-limiting illustrations of the invention.

EXAMPLE 1

A mixture of (3S)-1,2,3,4-tetrahydroisoquinoline-3-carboxylic acid VII (1 part by weight) and triphosgene [bis(trichloromethyl)carbonate](0.7 part by weight) in Solvent 1 (7 volumes) is heated under reflux for 3–5 hours, then cooled and distilled under a vacuum.

Tert-butylamine (1.8 parts by weight) is added over a period of approximately 2 hours to the residue taken up in Solvent 2 (10 volumes) which has been cooled to 0–5° C. The whole is agitated for 2–5 hours at ambient temperature and then the organic phase is extracted with water and HCl. The separated aqueous phase is rendered basic with sodium hydroxide; the solid so obtained is filtered and washed with water and dried to give (S)-N-tert-butyl-1,2,3,4-tetrahydroisoquinoline-3-carboxyamide I.

The yields as a function of Solvents 1 and 2 and as a function of the amounts of acid VII are given in the following Table which shows that, unlike the situation encountered when THF is used, the yield remains substantially unchanged when dioxane is used.

TABLE 1

| Sample | Solvent 1/Solvent 2 | Yield (5 g of VII) | Yield (100 g of VII) |
| --- | --- | --- | --- |
| A | AcOEt/AcOEt | <20% | — |
| B | Toluene/Toluene | <7% | — |
| C | THF/THF | 80% | 30% |
| D | THF/CH$_2$Cl$_2$ | 85% | 56% |
| E | THF/Toluene | 82% | 64% |
| F | Dioxane/Toluene | 84% | 85% |

EXAMPLE 2

A solution of triphosgene (75 kg) dissolved in dioxane (200 l) is added dropwise, with agitation, over a period of 2 hours to a mixture of acid VII (100 kg) in dioxane (300 l) heated to reflux. After one hour at that temperature, the whole is cooled to 40° C. and distilled to leave a residue. The residue is taken up in toluene (200 l) and the whole is distilled to leave a residue which is again taken up in toluene (800 l). Cooling is then carried out to 0–5° C. and a solution of tert-butylamine (177 l) is added over a period of approximately 2 hours.

Agitation is effected for a further one hour at the same temperature and then a solution of NaCl (50 kg) in water (1000 l) is added; the organic phase is extracted with water (1000 l) and acetic acid (100 l), treated with charcoal, filtered and rendered basic with sodium hydroxide. The solid so obtained is filtered, washed with water and dried to give 107.5 kg of (S)-N-tert-butyl-1,2,3,4-tetrahydroisoquinoline-3-carboxyamide I (yield 82%) in the form of a white crystalline powder, m.p.=93.5–97° C., purity=99.6% (HPLC).

What is claimed is:

1. A process for the production of (S)-N-tert-butyl-1,2,3,4-tetrahydroisoquinoline-3-carboxyamide, comprising:
    a) reacting (3S)-1,2,3,4-tetrahydroisoquinoline-3-carboxylic acid with triphosgene in dioxane to form an N-carboxyanhydride of the following formula

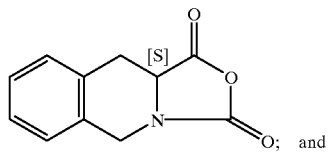

b) reacting the N-carboxyanhydride with tert-butylamine in toluene to produce the (S)-N-tert-butyl-1,2,3,4-tetrahydroisoquinoline-3-carboxyamide.

2. The process of claim 1, wherein step a) is carried out at temperatures within the range of from +20 to +105° C.

3. The process of claim 1, wherein the (3S)-1,2,3,4-tetrahydroisoquinoline-3-carboxylic acid is reacted in step a) at an initial concentration of from 0.3 to 2.0 m/l.

4. The process of claim 1, wherein the (3S)-1,2,3,4-tetrahydroisoquinoline-3-carboxylic acid is reacted in step a) at an initial concentration of from 0.5 to 1.5 m/l.

5. The process of claim 1, wherein the (3S)-1,2,3,4-tetrahydroisoquinoline-3-carboxylic acid is reacted in step a) with from 0.3 to 0.2 equivalents of triphosgene.

6. The process of claim 1, wherein the (3S)-1,2,3,4-tetrahydroisoquinoline-3-carboxylic acid is reacted in step a) with triphosgene under reflux.

7. The process of claim 1, wherein step b) is carried out at temperatures within the range of from −20 to +30° C.

8. The process of claim 1, wherein the N-carboxyanhydride is reacted in step b) with from 1 to 10 equivalents of tert-butylamine.

9. The process of claim 1, wherein the (S)-N-tert-butyl-1,2,3,4-tetrahydroisoquinoline-3-carboxyamide product is isolated by crystallization.

10. The process of claim 1, wherein step b) is carried out at temperatures within the range of from −10 to +5° C.

11. The process of claim 1, wherein the N-carboxyanhydride is reacted in step b) with from 3 to 5 equivalents of the tert-butylamine.

12. A process for the production of (S)-N-tert-butyl-1,2,3,4-tetrahydroisoquinoline 3-carboxyamide, comprising:
    a) reacting (3S)-1,2,3,4-tetrahydroisoquinoline-3-carboxylic acid at an initial concentration of 0.3 to 2 m/l. with from 0.3 to 1.2 equivalents of triphosgene, in dioxane and at temperatures within the range of from +20° to 105° C., to form an N-carboxyanhydride of the following formula

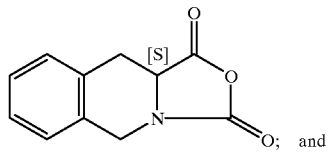

b) reacting the N-carboxyanhydride with tert-butylamine in toluene to produce the (S)-N-tert-butyl-1,2,3,4-tetrahydroisoquinoline-3-carboxyamide.

13. The process of claim 12, wherein the (3S)-1,2,3,4-tetrahydroisoquinoline-3-carboxylic acid is reacted in step a) with triphosgene under reflux.

14. A process for the production of (S)-N-tert-butyl-1,2,3,4-tetrahydroisoquinoline-3-carboxyamide, comprising:
   a) reacting (3S)-1,2,3,4-tetrahydroisoquinoline-3-carboxylic acid with triphosgene in dioxane to form an N-carboxyanhydride of the following formula

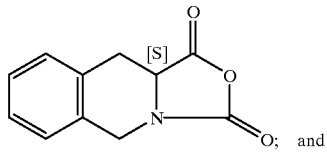

O; and b) reacting the N-carboxyanhydride with from 1 to 10 equivalents of tert-butylamine, in toluene and at temperatures within the range of from −20° to 30° C., to produce the (S)-N-tert-butyl-1,2,3,4-tetrahydroisoquinoline-3-carboxyamide.

15. A process for the production of (S)-N-tert-butyl-1,2,3,4-tetrahydroisoquinoline-3-carboxyamide, comprising:
   a) reacting (3S)-1,2,3,4-tetrahydroisoquinoline-3-carboxylic acid at an initial concentration of 0.3 to 2 m/l. with from 0.3 to 1.2 equivalents of triphosgene, in dioxane and at temperatures within the range of from +20° to 105° C., to form an N-carboxyanhydride of the following formula

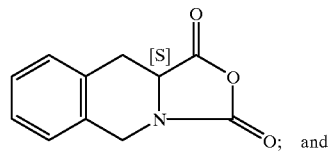

O; and b) reacting the N-carboxyanhydride with from 1 to 10 equivalents of tert-butylamine, in toluene and at temperatures within the range of from −20° to 30° C., to produce the (S)-N-tert--butyl-1,2,3,4-tetrahydroisoquinoline-3-carboxyamide.

16. The process of any of claims 12, 14 or 15, wherein the (3S)-1,2,3,4-tetrahydroisoquinoline-3-carboxylic acid is reacted in step a) with triphosgene under reflux.

* * * * *